United States Patent [19]

Takeda et al.

[11] 4,349,541

[45] Sep. 14, 1982

[54] ANTI-TUMOR PREPARATION AGAINST CERTAIN TUMORS AND PROCESS FOR PREPARING THE SAME

[75] Inventors: Yasuhisa Takeda, Yokohama; Takashi Matsuno, Omiya; Mihoko Ohtaka, Tokyo; Hiroki Mitsui, Iruma; Tsutomu Kawaguchi, both of Tsurugashimamachi; Hisako Masuda, Tokyo; Hiroshi Okazaki, Sayama; Mitsuaki Handa, Kamifukuoka; Yutaka Sugawara, Omiya; Haruki Ogawa, Chofu, all of Japan

[73] Assignee: Chugai Seiyaku Kabushiki Kaisha, Tokyo, Japan

[21] Appl. No.: 42,419

[22] Filed: May 25, 1979

[30] Foreign Application Priority Data

May 29, 1978 [JP] Japan .................................. 53-63418

[51] Int. Cl.$^3$ ..................... A61K 37/00; A61K 35/74
[52] U.S. Cl. ........................................ 424/95; 424/93
[58] Field of Search .................................. 424/93, 95

[56] References Cited

U.S. PATENT DOCUMENTS 3,477,914 11/1969 Okamoto et al. ..................... 424/93
3,729,554  4/1973 Suzuki et al. ........................ 424/93

Primary Examiner—Jerome D. Goldberg
Attorney, Agent, or Firm—Browdy and Neimark

[57] ABSTRACT

An anti-tumor preparation containing cells of *Streptococcus equisimilis* and a process for preparing the preparation which comprises subjecting the cells to heat treatment in a salt solution with or without penicillin treatment.

3 Claims, No Drawings

ANTI-TUMOR PREPARATION AGAINST CERTAIN TUMORS AND PROCESS FOR PREPARING THE SAME

This invention relates to an anti-tumor preparation containing cells of bacterial belonging to *Streptococcus hemolyticus*, particularly, *Streptococcus equisimilis*, and a process for preparing the same.

It has been clinically shown that the infection with bacteria belonging to *Streptococcus hemolyticus* having a β-hemolytic activity exhibits a certain anti-cancer activity. However, it has been also known that the bacteria is a pathogen to cause erysipelas, etc., and that its activity against certain tumors is extremely unstable, that is, is easily inactivated by heating or other treatment. For these reasons, it has not been possible to use the bacteria living cells for treatment of such tumors. Various techniques have been tried in order to apply the bacteria belonging to *Streptococcus hemolyticus* to treatment of cancer. For example, one method comprises suspending living cells of bacteria belonging to *Streptococcus hemolyticus* in Bernheimer's basal medium (referred to as "BBM" hereunder), adding penicillin to the suspension at an extremely high concentration and heating the mixture U.S. Pat. No. 3,477,914. Other methods have been reported in U.S. Pat. No. 3,729,554 Japanese Patent Publication No.

During their study, the inventors have found that the strain of *Streptococcus equisimilis* has an activity against certain tumors far stronger than that of conventional strain of *Streptococcus hemolyticus*. Especially, a pharmaceutical preparation derived from the specific strain of *Streptococcus equisimilis* (ATCC 21597) has been confirmed to have a high activity against MH 134 tumor, against which a pharmaceutical preparation containing cells of known *Streptococcus hemolyticus* has not shown any activity, and to exhibit an activity even by the intraperitoneal administration against certain solid tumors, against which a conventional preparation exhibits a little or no anti-tumor activity by the intraperitoneal administration. In addition, the activity against certain tumors of the strain of *Streptococcus equisimilis* is relatively resistant to heat and, therefore, even cells of the strain killed by heat treatment have sufficient activity for a pharmaceutical preparation.

The inventors continued study based on such facts to complete this invention.

A strain of *Streptococcus equisimilis* which is useful for this invention includes, for example, the strain ATCC 21597. This strain has been deposited with the Fermentation Research Insittute (FRI), Agency of Industrial Science and Technology, Japan under the Deposit Application Acceptance No. 4509 and with ATCC under Group-C *Straptococcus* sp. ATCC 21597.

The microbilogical characteristics of the strain are shown below and are equivalent to those of *Streptococcus equisimilis* indicated in Bergey's "Manual of Determination Bacteriology", 8th Edition.

(1) Morphological Characteristics

Cell is spherical or egg-like figure having a diameter of up to 2 μm and forms a typical chain in Todd Hewitt medium.

(2) Physiological Characteristics (1) Type of Hemolysis: β-hemolysis
(2) Serological Classification by Lancefield: C-group
(3) Catalase Activity: negative
(4) Growth at 10° C. and 45° C.: negative
(5) Growth at a pH of 9.6: negative
(6) Growth in a 10% bile-containing medium: positive
(7) Growth in a 40% bile-containing medium: negative
(8) Growth in a 6.5% NaCl-containing medium: negative
(9) Hydrolysis of hippuric acid: negative
(10) Fermentation of sugars (Production of acid from carbohydrates)

TABLE 1

| | | | |
|---|---|---|---|
| glycerin: | positive | trehalose: | positive |
| lactose: | positive | glycerol: | positive |
| meltose: | positive | salicin: | negative |
| manitol: | negative | glucose: | positive |
| raffinose: | negative | sucrose: | positive |
| inositol: | positive | inulin: | negative |
| arabinose: | negative | sorbitol: | negative |
| xylose: | positive | | |

(11) Arginine-decarboxylase activity: positive
(12) Ornithine-decarboxylase activity: negative
(13) Lysine-decarboxylase activity: negative
(14) Assimilation of a salt of citrate: negative
(15) Production of hydrogen sulfide: negative
(16) Production of indole: negative
(17) Urease activity: negative
(18) ONPG test (O-nitrophenyl-β-D-galactopyranoside test): negative
(19) Boges-Pros Kauer test: negative
(20) Dissolution of cellulose: weakly positive The cultivation of the bacteria of *Streptococcus equisimilis* according to this invention is carried out for example, by the use of a bouillon medium or a 3–5% yeast extract medium at around 37° C. The cultivation time is usually 18–20 hours, but it varies somewhat depending upon particular medium, used cell counts inoculated, etc. After the cultivation, cells are separated from the culture broth by a conventional technique, such as centrifugation, washed with a proper liquid such as physiological saline and used for the purpose of this invention.

When this invention is practiced, a conventional technique for formulating a pharmaceutical preparation containing cells of *Streptococcus hemolyticus* can be applied. That is, cells of *Streptococcus equisimilis* are suspended in a salt solution such as BBM (a solution prepared by dissolving maltose, $KH_2PO_4$ and $MgSO_4 7H_2O$ in distilled water and adjusting its pH to 6.8–7.0 with sodium hydroxide), and penicillin is added to the suspension in an amount such that the concentration of penicillin in the suspension is above 25,000, more preferably, 26,000–60,000 units/ml. The mixture is allowed to stand at 30°–38° C. for longer than 10 minutes, more preferably, 10–30 minutes and then subjected to heat treatment at 40°–50° C. for 20–40 minutes.

Although BBM is a desirable salt solution, a phosphoric acid buffer-containing physiological saline or a physiological saline alone may also be used as the salt solution.

Since the activity against certain tumors of *Streptococcus equisimilis* is relatively resistant to heat, the cells are suspended in a salt solution such as BBM, a phosphoric acid buffer-containing physiological saline or a physiological saline and the suspension is subjected to heat treatment at 65°–100° C. for 5–30 minutes to use the cells for preparation against certain tumors.

The thus obtained preparation can be clinically used as it is, or it can be stored for a long period of time after lyophilization. When the lyophilization is made, amino acid such as methionine, arginine, ornithine, cysteine, aspartic acid, glutamic acid, etc. or a sugar such as sucrose, maltose, raffinose, lactose, dextran, soluble starch, etc. may be desirably incorporated to the preparation.

This invention is further illustrated by the following Examples and Experiments.

EXAMPLE 1

The strain of *Streptococcus equisimilis (ATCC* 21597) was inoculated in the bouillon medium (100 ml.) and precultivated at 37° for 20 hours. The culture broth was then inoculated in a 5% yeast extract medium (2 l.) and cultivated at 37° C. for 20 hours. Then, the culture broth was centrifuged to collect the cells. The cells were suspended in physiological saline (40 ml) and, after adding 10% hydrogen peroxide aqueous solution (4 ml.) and thoroughly mixing, the mixture was allowed to stand at 0° for 30 minutes. The mixture was centrifuged to collect the cells and physiological saline (30 ml.) was added to the cells and the cells were washed twice by adding physiological saline (30 ml.) to the cells and recovering the cells by centrifugation.

The cells were suspended to BBM (90 ml.) to form a cocci-suspension in BBM. The 1:20 diluted solution of the cocci-suspension with physiological saline has an absorption of 0.460 at 660 nm by Hitachi spectrophotometer Model 101. To the cocci-suspension in BBM (85 ml.) was added a sodium benzylpenicillin (17 ml.: $1.6 \times 10^5$ units/ml.) and the mixture was allowed to stand at 37° C. for 20 minutes and heated at 45° C. for 30 minutes to give a cocci-suspension.

To the cocci-suspension (102 ml.) was added a solution (102 ml.) of penicillin and DL-methionine (potassium benzylpenicillin $1.08 \times 10^5$ units/ml.; 1.0% DL-methionine aqueous solution), followed by mixing. The suspension was poured into ninety vials in an amount of 2 ml. each, lyophilized and sealed in dry air under atmospheric pressure to give 90 vials containing 5 mg of dried cells each.

EXAMPLE 2

The strain of *Streptococcus equisimilis* ATCC 21597 was cultivated as in Example 1 and the culture broth (2.1 l.) was centrifuged to collect the living cells. The cells were washed twice by adding physiological saline to the cells and centrifuging the mixture.

The cells were suspended in BBM (108 ml.) to give a cocci-suspension in BBM. The diluted suspension (1:20) of the cocci-suspension in BBM with physiological saline had an absorption of 0.400 to 600 nm by Hitachi spectrophotometer Model 101. The cocci-suspension in BBM was heated on a water bath at 90° C. for 10 minutes and cooled with ice.

To the suspension (102 ml.) was added a 10% DL-methionine aqueous solution (102 ml.) and, after thoroughly mixing, the suspension was poured into ninety vials in an amount of 2 ml. each. The suspension in the vials was lyophilized and each vials was sealed in a dry air under atmospheric pressure to give 90 vials, each of which contained 5 mg of dried cells.

EXAMPLE 3

By the procedure similar to that of Example 2, a cocci-suspension in BBM from the strain of *Streptococcus equisimilis* was obtained. The suspension was heated on a water bath at 65° C. for 10 minutes and lyophilized as in Example 2.

EXPERIMENT 1

MH 134 tumor cells were subcateneously inoculated in the back of male C3H/HeN mice (3 weeks old) in a count of $10^6$ cells per each mouse. Three days after the inoculation, each mouse was intravenously administered 5 times every second day with a suspension of the lyophilized dry powder obtained in Example 1 in physiological saline in a dose of 0.1 mg in terms of dry cell weight. Twenty days after the inoculation, the weight of the tumor was measured. For positive control, the cells of the Su-strain of *Streptococcus pyogenes* (ATCC 21068) which had been treated as in Example 1 and suspended in physiological saline was subjected to the same test.

The results are shown in Table 2. As is clearly shown in Table 2, the preparation from the cells of *Streptococus equisimilis* (ATCC 21597) exhibited a remarkable activity against MH 134 tumor-cells, while the preparation from Su-strain of *streptococcus pyogenes* had very little activity.

TABLE 2

| Type of Preparation | Number of Mice (heads) | Tumor Weight (g) Average ± S.E.* | Percent Depression |
|---|---|---|---|
| *Streptococcus equisimilis* ATCC 21597 strain | 10 | 0.24 ± 0.07** | 81.8 |
| *Streptococcus pyogenes* Su-strain | 10 | 1.03 ± 0.19 | 22.0 |
| Control (no administration) | 11 | 1.32 ± 0.21 | — |

*S.E.: Standard errors
**P < 0.001 (by t-test based on the control)

EXPERIMENT 2

BAMC 1 tumor cells were subcataneously inoculated in the back of female BALB/cAnN mice (6 weeks old) in a count of $10^6$ cells per mouse. Three days after the inoculation, each mouse was intravenously or intraperitoneally administered 5 times every second day with a suspension of lyophilized dry powder obtained in Example 1 in physiological saline in a dose of 0.1 mg in terms of dry cell weight. Twenty one days after the inoculation, the tumor weight of each mouse was measured. As a positive control, a preparation formulated as in Example 1 from Su-strain of *Streptococcus pyogenes* was suspended in physiological saline and used in the same test.

The results are shown in Table 3 below. As is clearly shown, the anti-tumor activity of the preparation from the strain of *Streptococcus equisimilis* (ATCC 21597) against BAMC 1 tumor is far superior to that from Su-strain of *Streptocuccus pyogenes*.

TABLE 3

| Type of Preparation | Route of Administration | Number of Mice (heads) | Tumor Weight (g) Average ± S.E. | Percent Depression |
|---|---|---|---|---|
| *Streptococcus equisimilis* ATCC 21597 strain | i.v. | 10 | 0.72 ± 0.01 | 65.9 |
|  | i.p. | 11 | 1.07 ± 0.14 | 48.2 |
| *Streptococcus pyogenes* Su-strain | i.v. | 10 | 1.00 ± 0.11 | 51.1 |
|  | i.p. | 10 | 1.84 ± 0.10 | 10.4 |

TABLE 3-continued

| Type of Preparation | Route of Administration | Number of Mice (heads) | Tumor Weight (g) Average ± S.E. | Percent Depression |
|---|---|---|---|---|
| Control (no administration) | | 11 | 2.08 ± 0.29 | — |

EXPERIMENT 3

Enrlich tumor cells were subcutaneously inoculated in the back of nude mice (5 weeks old: half of them being male) in a count of $10^6$ cells per mouse. Three days after the inoculation, each mouse was intravenously or intraperitoneally administered 5 times every second day with a suspension of lyophilized dry powder obtained in Example 1 in physiological saline in a dose of 0.1 mg in terms of dry cell weight. Twenty one days after the inoculation, the tumor weight of each mouse was measured. As a positive control, a preparation formulated as in Example 1 from Su-strain of *Streptococcus pyogenes* was suspended in physiological saline and used in the same test.

The results are shown in Table 4 below. As is clearly shown, the anti-tumor activity of the preparation from the strain of *Streptococcus equisimilis* (ATCC 21597) against Ehrlich tumor is superior to that from Su-strain of *Streptococcus pyogenes*.

TABLE 4

| Type of Preparation | Number of Mice (heads) | Tumor Weight (g) Average ± S.E. | Percent Depression |
|---|---|---|---|
| *Streptococcus equisimilis* ATCC 21597 strain | 9 | 0.50 ± 0.04* | 89.0 |
| *Streptococcus pyogenes* Su-strain | 9 | 1.14 ± 0.23* | 74.8 |
| Control (no adminstration) | 12 | 4.53 ± 0.50 | — |

*P<0.001 (by t-test based on the control)

EXPERIMENT 4

Meth A tumor cells were subcataneously inoculated in the back of male BALB/cAnN mice (6 weeks old) in a count of $10^6$ cells per mouse. Three days after the inoculation, each mouse was intravenously or intraperitoneally administered 5 times every second day with a suspension of lyophilized dry powder obtained in Example 1 in physiological saline in a dose of 0.1 mg of terms of dry cell weight. Twenty one days after the inoculation, the tumor weight was of each mouse measured.

The results are shown in Table 5 below. As is clearly shown, the anti-tumor activity of the preparation from the strain of *Streptococcus equisimilis* (ATCC 21597) against Meth A tumor is excellent.

TABLE 5

| Type of Preparation | Number of Mice (heads) | Tumor Weight (g) Average ± S.E. | Percent Depression |
|---|---|---|---|
| *Streptococcus equisimilis* ATCC 21597 strain | 10 | 0.57 ± 0.12* | 76.8 |
| Control (no administration) | 10 | 2.46 ± 0.42 | — |

*P<0.001 (by t-test based on the control)

EXPERIMENT 5

By the procedure similar to that of Experiment 1, male C3H/HeN mice (6 weeks old) were administered the pharmaceutical preparation obtained in Example 1 or Example 2 from the strain *Streptococcus equisimilis* (ATCC 21597) and the anti-tumor activity of the preparations against MH 134 tumor was comparatively observed by weighing the tumor 19 days after the inoculation.

The results are shown in Table 6 below. Both preparations exhibit excellent anti-tumor activity against MH 134 tumor.

TABLE 6

| Type of Preparation | Number of Mice (heads) | Tumor Weight (g) Average ± S.E. | Percent Depression |
|---|---|---|---|
| Preparation of Example 1 | 10 | 0.27 ± 0.06* | 65.4 |
| Preparation of Example 2 | 10 | 0.27 ± 0.05* | 65.4 |
| Control (no administration) | 10 | 0.78 ± 0.15 | — |

*P<0.01 (by t-test based on the control)

EXPERIMENT 6

By the procedure similar to that of Experiment 1, male BALB/cAnN Crj mice (5 weeks old) were administered with the preparation obtained in Example 1, Example 2 or Example 3 from the strain *Streptococcus equisimilis* (ATCC 21597) and the anti-tumor activity between the preparations against Meth A tumor was compared by weighing the tumor 19 days after the inoculation.

The results are shown in Table 7 below. All of the preparations exhibit excellent anti-tumor activity against Meth A tumor.

TABLE 7

| Type of Preparation | Number of Mice (heads) | Tumor Weight (g) Average ± S.E. | Percent Depression |
|---|---|---|---|
| Preparation of Example 1 | 9 | 0.43 ± 0.08* | 85.1 |
| Preparation of Example 2 | 9 | 0.42 ± 0.15* | 85.5 |
| Preparation of Example 3 | 9 | 0.75 ± 0.18* | 74.0 |
| Control (no administration) | 9 | 2.89 ± 0.25 | — |

*P<0.001 (by t-test based on the control)

EXPERIMENT 7

Each of the preparations obtained in Examples 1, 2 and 3 was suspended in physiological saline and, after inactiviating penicillin contained in the suspension of the preparation of only Example 1 by treatment with penicillinase, each suspension was mixed in a conventional way with horse defibrinated blood agar. The mixture was shaped into a plate, cultivated at 37° C. for 48 hours. After the cultivation, the living cells were counted.

By this test, it was confirmed that none of the preparations contained living cells.

We claim:

1. A preparation effective against tumors such as MH 134, BAMC 1, Ehrilich tumor, and Meth A tumor, comprising a pharmaceutically acceptable carrier containing killed cells of *Streptococcus equisimilis* ATCC 21597 in an effective amount.

2. A preparation according to claim 1, in lyophilized form.

3. A preparation according to claim 2, containing approximately 5 mg of dried cells.

* * * * *